(12) United States Patent
McCreesh et al.

(10) Patent No.: US 8,549,629 B1
(45) Date of Patent: Oct. 1, 2013

(54) CLASSIFICATION AND IDENTIFICATION OF COMPUTER USE

(75) Inventors: Martin McCreesh, Dunleer (IE); Christopher Jerome Schnurr, Londonderry (GB); Frank Maurer, Barnesmore (IE)

(73) Assignee: Verint Americas Inc., Alpharetta, GA (US)

( * ) Notice: Subject to any disclaimer, the term of this patent is extended or adjusted under 35 U.S.C. 154(b) by 601 days.

(21) Appl. No.: 12/725,166

(22) Filed: Mar. 16, 2010

Related U.S. Application Data (60) Provisional application No. 61/160,548, filed on Mar. 16, 2009.

(51) Int. Cl.
*G06F 21/00* (2013.01)

(52) U.S. Cl.
USPC .......................................................... 726/22

(58) Field of Classification Search
None
See application file for complete search history.

(56) References Cited

U.S. PATENT DOCUMENTS

| | | | |
|---|---|---|---|
| 7,185,367 B2 | 2/2007 | Munson | |
| 7,237,264 B1 | 6/2007 | Graham et al. | |
| 2004/0103296 A1* | 5/2004 | Harp et al. | 713/200 |
| 2004/0187037 A1 | 9/2004 | Checco | |
| 2005/0183143 A1* | 8/2005 | Anderholm et al. | 726/22 |
| 2008/0047017 A1 | 2/2008 | Renaud | |
| 2008/0141349 A1 | 6/2008 | Lyle et al. | |

\* cited by examiner

*Primary Examiner* — David Pearson
(74) *Attorney, Agent, or Firm* — Meunier Carlin & Curfman (57) ABSTRACT

Methods, programs, and systems for classifying and monitoring user-computer interactions include monitoring keystroke characteristics, mouse characteristics, and application frequency and garnering associated data. Metrics associated with the monitored data are then analyzed and used for a several business and security applications: Security-Impersonation, Security-Profiling, Business-Training, and Business-Application Development. The methods of the present disclosure enable greater insight into user-computer interactions.

20 Claims, 4 Drawing Sheets

*Sample data of user running an email client over a period of 12 days.*

| Date | Duration | Mouse | KeyPress | User | Computer |
|---|---|---|---|---|---|
| 20080305 | 8 | 1 | 0 | 5 | 7 |
| 20080307 | 18 | 1 | 0 | 5 | 7 |
| 20080308 | 2 | 0 | 0 | 5 | 7 |
| 20080310 | 9 | 1 | 1 | 5 | 7 |
| 20080311 | 7 | 1 | 5 | 5 | 7 |
| 20080312 | 13 | 1 | 20 | 5 | 7 |
| 20080313 | 5 | 1 | 0 | 5 | 7 |
| 20080314 | 7 | 1 | 8 | 5 | 7 |
| 20080315 | 29 | 1 | 60 | 5 | 7 |
| 20080317 | 24 | 1 | 54 | 5 | 7 |
| 20080318 | 6 | 1 | 2 | 5 | 7 |

FIGURE 1

*Sample data of user running an email client over a period of 12 days.*

| Date | Duration | Mouse | KeyPress | User | Computer |
|------|----------|-------|----------|------|----------|
| 20080305 | 8 | 1 | 0 | 5 | 7 |
| 20080307 | 18 | 1 | 0 | 5 | 7 |
| 20080308 | 2 | 0 | 0 | 5 | 7 |
| 20080310 | 9 | 1 | 1 | 5 | 7 |
| 20080311 | 7 | 1 | 5 | 5 | 7 |
| 20080312 | 13 | 1 | 20 | 5 | 7 |
| 20080313 | 5 | 1 | 0 | 5 | 7 |
| 20080314 | 7 | 1 | 8 | 5 | 7 |
| 20080315 | 29 | 1 | 60 | 5 | 7 |
| 20080317 | 24 | 1 | 54 | 5 | 7 |
| 20080318 | 6 | 1 | 2 | 5 | 7 |

CLASSIFICATION AND IDENTIFICATION OF COMPUTER USE

RELATED APPLICATIONS

This application claims the benefit of U.S. provisional application entitled "CLASSIFICATION AND IDENTIFICATION OF COMPUTER USE" having Ser. No. 61/160,548 filed on Mar. 16, 2009, all of which is entirely incorporated herein by reference.

FIELD

The disclosure relates generally to computer systems and the user's interaction with those computer systems. More specifically the disclosure relates to monitoring, understanding, and improving user-computer interactions.

BACKGROUND

As the world continues to advance technologically, efficient and secure work on digital media is becoming very important. Efficiency has become difficult to measure with the increasing ease of access to the internet, as well as normal misuse, and abnormal malfunctions within the program. Security is also difficult to maintain in an environment where every person and machine is not directly supervised in addition to any unauthorized remote access via the internet.

Inefficiencies among the assets in a company waste time, money, and resources. U.S. Pat. No. 7,185,367 describes a disclosure that uses the statistical analysis of the differences between normal behaviors of any program including the operating system, and then compares this to the current run to determine any anomalies, which could be unauthorized, abusive, productive, or unproductive use of the Computer system. Therefore, if the Computer system is not operating properly then the disclosure records and notifies the correct people about the problem. The cause of improper operation could range from (but is not limited to) improper inputs from the user, to use of the program for functions it is not designed for, to malfunctioning of the code.

Security of digital media has a variety of prior art covering a wealth of options including traditional virus protection, but more specifically options dealing with the behavior associated with the system. For example, U.S. Patent Application Publication No. 2008/0047017 assesses the risks of users based on questions that quiz the user's behavior. The user is presented questions, and the computer dynamically assesses changes to the user's security level as a result of the information provided by the responses. Likewise, U.S. Patent Application Publication No. 2008/0141349 determines whether a user should be routed to the generated content based on the content of the computer associated with the network.

In a different method, U.S. Pat. No. 7,723,264 prevents misuse conditions on a data network by analyzing variables such as the state of the network and/or target, the response/reaction of the network and/or target, and/or the fingerprint of the target. The disclosure is looking for the receipt of suspicious data transmissions by a network node, originating by another network node.

Keyboard use in terms of keystroke rate and timings of speed between different keys on the keyboard has been widely used in biometric systems to provide patterns of keystrokes which can be associated with a particular user (such as in U.S. Patent Application Publication No. 2004/0187037 A1). However, the number of key presses that occur within a graphical window on screen, or those that occur within a component of this window, is also a useful measurement of user behaviour. Further, the referenced patent only monitors keystrokes during log-in events.

Methods which track user-computer interactions throughout the duration of the interaction are needed. Further, the metrics for monitoring log-in time events can not fully capture all interaction. The referenced disclosure does not provide a method for tracking application switches, application usage frequency, mouse clicks within an application, or keystrokes within an application. These limitations do not enable the referenced patent to enable a greater insight into user-computer interactions.

Further, there is not a system which analyzes the way an individual computer operating system is used and interacted with by its user which allows objective analysis and measurement of anomalous behavior patterns.

Further, there is not a system that allows managers the ability to both analyze efficiency and security of a network or computer at the same time. There is a need to be able to measure and classify the user behavior of the computer in terms of this user's own individual preferences and approaches to the user interface.

SUMMARY

The method, program, and system illustrated and described herein have several features, no single one of which is solely responsible for its desirable attributes. Without limiting the scope as expressed by the description that follows, its more prominent features will now be discussed briefly. After considering this discussion, one will understand how the features of the invention provide for the monitoring, understanding, or modifying of user-computer interactions.

A computer user interacts with a computer system in a number of different quantifiable ways. Each of these interactions produces an independent stream of events. These different streams can be combined to create a unique user computer interaction fingerprint, which can be used to classify a user's behaviour. The classification allows identification of different types of users, and of identifying outlying behaviour both within individuals and across groups of individuals. The metrics associated with a user profile may be used to grant greater insight and change the way in which that user interacts with the computer.

In some examples, a monitoring system comprises a computer system and a plurality of input devices coupled to the computer system, wherein the input devices comprise a keyboard and a mouse. The computer system is configured to receive a user identifier associated with a user operating the computer system, associate a usage session of the computer system with the user based on the user identifier, monitor an application executing on the computer system during the usage session to determine a duration the application is in focus and a frequency of change in the focus of the application, monitor keystroke characteristics and mouse characteristics of the user associated with the application during the usage session, and generate a usage profile based on the duration the application is in focus, the frequency of change in the focus of the application, the keystroke characteristics, and the mouse characteristics monitored during the usage session, wherein the usage profile comprises an indication of usage characteristics of the user for the application.

BRIEF DESCRIPTIONS OF THE DRAWINGS

The accompanying drawings, which are incorporated in and constitute a part of this specification, illustrate several embodiments of the disclosure and together with the description, serve to explain the principles of the disclosure. For a more complete understanding of the present embodiment, and the advantages thereof, reference is now made to the following brief descriptions, which are to be taken in conjunction with the accompanying figures, in which like reference numerals indicate like features.

DETAILED DESCRIPTION

The detailed description set forth below in connection with the appended drawings is intended as a description of exemplary embodiments in which present invention can be practiced. The term "exemplary" used through this description means "serving as an example, instance, or illustration," and should not necessarily be construed as preferred or advantageous over other embodiments. The detailed description included specific details for the purpose of providing a thorough understanding of the present invention. However, it will be apparent to those skilled in the art the present invention may be practiced without these specific details. In some instances, well known structures and devices are shown in block diagrams form in order to avoid obscuring the concepts of the present invention.

A typical user/computer interaction will consist of input from the user, in terms of keyboard, mouse (or other direct manipulation input (DMI) device), and output to the user from the computer, in terms of graphical screen change, sound, or other computer device manipulation. Each interaction type can be seen as a style of interaction. The present invention takes into account the usage styles for keyboard, mouse/DMI, window frequency, and duration, but could also be applied to additional data streams to augment the data analysis (such as call data from telephony, file system behaviour, network activity).

Several methods for monitoring and classifying user-computer interactions are presented. There may be many other interactions known to those with ordinary skill in the art.

If a screen opens a window, and few keystrokes are recorded while it is open, then it is likely that the user may be looking, or reading the content of this window rather than writing or otherwise interacting with it.

If the keystroke count is very high within this window for a particular set of keys, it is likely that the user is holding down these keys for periods of time, since the keystroke events will repeat rapidly when a key is pressed. Key repeat behaviour may be symptomatic of game playing.

If the keystroke count is varied and sustained, then it is likely that the user is typing into the window on screen, rather than reading it.

Mouse use can be defined in terms of both clicks per window on screen and also movement per window on screen.

If a screen opens a window and few mouse clicks are performed, or only mouse wheel clicks are performed, then it may be that the user is scrolling through a document, or that the user does not use the mouse in this screen and instead may be familiar with all keyboard shortcuts required instead.

If a screen opens a window and mouse movement is high and mouse click is also high, then it is likely that the user may be manipulating objects on screen via the mouse. This may be a symptom of game playing, or a symptom of poor interface skills (using mouse repeatedly instead of more efficient tab key/shortcut key combinations).

If a screen opens a window and mouse events occur in short bursts, it is likely that the user may be using mouse only for menu items.

The screen frequency can be defined as the number of times a window is open on screen and the duration is the number of seconds for which this screen is open at each instance. The window frequency and duration are dependent on two factors: user preference, and intended design.

Particular users may use an application on screen for a particular task, which may not be the original intended use by the designers of the application (for example, using Microsoft Word to draw, or Notepad to write emails before copying into an email client).

Most applications have been designed to perform a particular task. Using them in the way the system originally intended can have a bearing on the window frequency. For example, notepad is designed as a screen to be used occasionally jotting down items for copy & pasting. Using notepad as originally designed, a user might show a high number of uses of notepad, each with a low over all duration, as they switch into the notepad screen/window, copy and/or paste, and then switch windows out again.

It is possible that the intended design window frequency may be the overall average window frequency score within an organisation, and the user preference frequency will be more closely associated with outlying windows frequency usage.

The session window frequency represents how often as a proportion of the entire days work, a particular window on screen has occurred. The session window frequency can be calculated in terms of the percentage of time spent in this window/screen as opposed to the percentage of time spent in all non-idle screens.

Secondly, the rate of window change can be determined against the session: the number of window changes in this application as a proportion of the total number of window changes in all applications for the entire days work.

As discussed above, the four data streams that are obtained using the current monitoring technology are as follows:

Duration of active window
Frequency of window change
Number of key presses in active window
Number of mouse clicks in active window
Mouse movement in an active window For any given application and individual, their computer use can be seen in terms of these four data streams. If monitored over a given time period, this computer use can be analysed in terms of a normal distribution curve: average scores for key press, window count, and mouse clicks in a given duration are calculated, along with standard deviations away from these scores.

Figure 1:
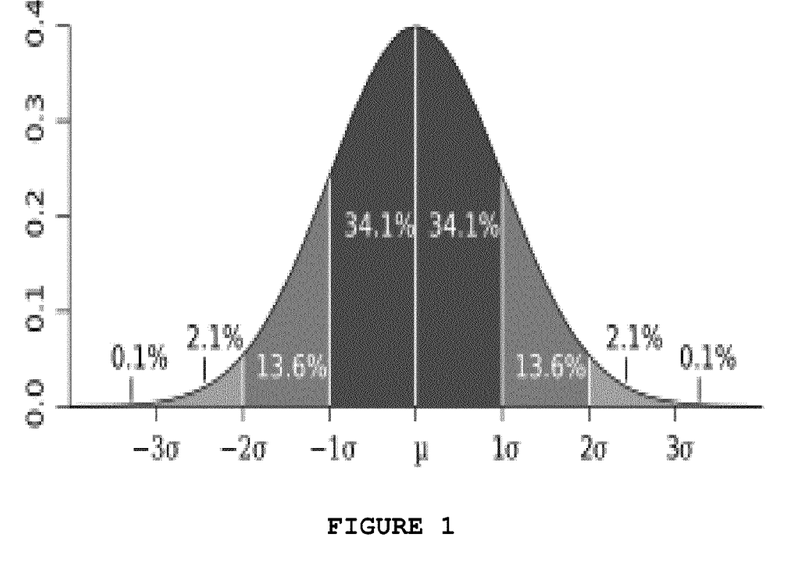
FIG. 1 illustrates a graphical view of a standard confidence interval.

Using the confidence intervals within standard deviation on a normalised distribution of FIG. 1, we can assume that any scores that occur outside of 2 standard deviations from the mean scores are statistically interesting for review, and can be classed as abnormal behaviour within the application (they account for only 5% of possible score).

Figure 2:
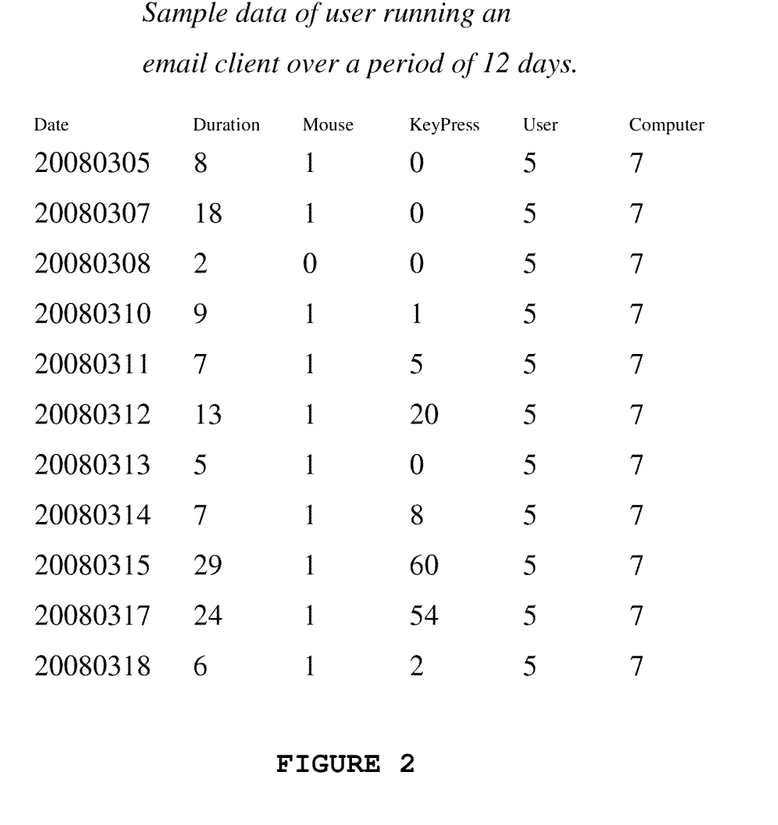
FIG. 2 is a chart of the exemplary data for a specific user on several different days.
Figure 3:
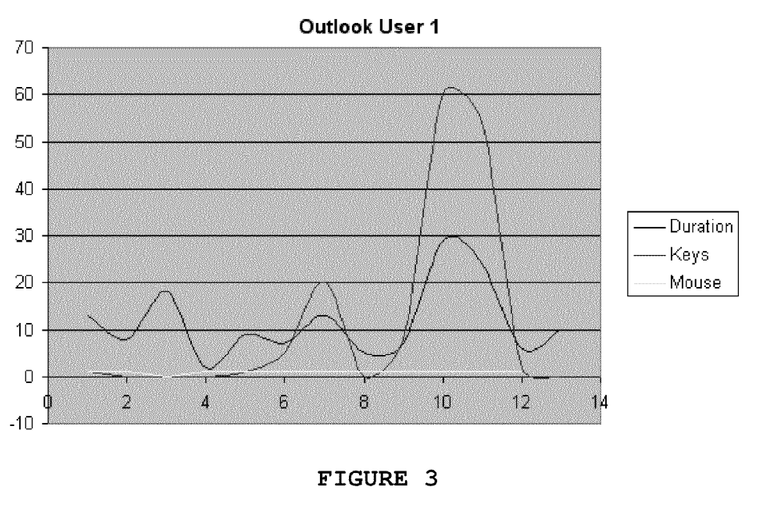
FIG. 3 illustrates the data from FIG. 2 in graphical form.

Graphing the data streams in FIG. 2, graph can be seen in FIG. 3, shows us how the different data streams interact with each other and change as the tasks being performed change.

Applying the 2 standard deviations from mean rule on the above data, we highlight the following portion of the original dataset:

| Date | Duration | Mouse | KeyPress | User | Computer |
|---|---|---|---|---|---|
| Mar. 15, 2008 | 29 | 1 | 60 | 5 | 7 |
| Mar. 17, 2008 | 24 | 1 | 54 | 5 | 7 |

Of interest here are days March 15 and March 17, where the key press data stream is very different to the rest of the time using this application. This demonstrates days where the activity in email was primarily composing emails, where as the other days, most time spent in this email client was spent reading. Note also that this user does not use the mouse at all during email use.

If we overlay this data with other applications for the same period of time, we can give an indication of how the peaks and troughs of different applications interact with each other, to highlight periods of work with different styles.

In the above example, the use of DEVENV, the principle work environment for this user, is as follows:

| Date | Duration | Mouse | KeyPress | User | Computer |
|---|---|---|---|---|---|
| Mar. 15, 2008 | 0 | 0 | 0 | 5 | 7 |
| Mar. 17, 2008 | 10 | 1 | 1 | 5 | 7 |

Thus, as predicted, when this user spends an abnormal amount of time in email, they are also spending an abnormal amount of time (in this case, practically zero) in their normal working environment.

This information can be used to highlight to supervisors when computer use is out of the ordinary. The reason behind this change in behaviour is more difficult to quantify, but highlighting this change is relatively simple to perform.

The statistical analysis shown above highlights the abnormal behaviour within a dataset of computer use. This can be applied in the following ways:

Change in computer use within an individual can be detected as soon as there is a body of data available for this user. Depending on the workload of this user, it could be as little as 1-2 days of background data to establish a pattern before abnormal use is highlighted Changes in individual computer use can be observed:
before and after training—highlighting training efficacy
start of project vs. end of project—highlighting boredom/stress levels or willingness to start/finish
start of week vs. end of week
Before/leading up to and after vacation—highlighting stress levels etc.

Where the average is applied to a group of users, the abnormal use becomes those users who are not conforming to the typical patterns of computer use within the group.

Changes in Team use can highlight:
Novice users
Expert users
Unproductive users

Although a good team lead/manager will already know the unproductive users, the data obtained on overlaying different applications for an individual highlights the applications that are being used on the unproductive user's computer. This could give additional context as to why these users are not up to speed with the rest of the group: it could be unproductive email/internet use, but equally it could highlight novice use of applications (such as, a user always loading Microsoft word to compose an email, instead of just using outlook, etc.).

The identification and classification of users from the abnormal scores on these data streams constitutes a unique and novel approach to monitoring, understanding, and modifying human computer interaction, which enhances usability measurement and human factors engineering.

The three behavioural styles (frequency, mouse, and keyboard use) can be seen as independent factors which each influence the overall duration spent within an application. That is, in general, a user could perform any one of the above behavioural styles with or without affecting any other of the behavioural styles. Typically, a combination of all of them can be used to describe different types of behaviour (reading, typing, browsing, game playing, etc) but each individual user will exhibit certain traits of the behaviour which identify their own particular approach to each application or the use of the computer in general. Thus, the different interaction streams combine to affect the overall time spent within each application.

Assuming that each of the above usability metrics are individual factors of computer use allows us to use factor analysis to identify particular patterns of behaviour in each application. For example, one set of users may use word with high keystroke and low mouse (writing documents), another low key press and high mouse scrolling (reading documents), a further group using low keystrokes, and high mouse click and scroll (potential web browsing inside a word document).

Using Factor analysis, we assign each of the behavioural styles as independent factors, which all have a degree of both interaction and effect on the dependent factor, time spent in application.

Each style is given a numerical value which is the user's average score per window for each application

| | Independent | | | Dependent |
|---|---|---|---|---|
| | KeyPress | Mouse | windowFreq | Duration |
| UserA | 23 | 5 | 10 | 400 |
| UserB | 31 | 2 | 15 | 300 |
| UserC | 5 | 12 | 3 | 250 |
| UserD | 12 | 10 | 12 | 200 |

The computer usage signature of each individual becomes their score, (best fit vector) on each particular application running on the desktop.

These metrics can be run against a group of users for a single application, or a single user for a single application over time.

Repeating against a group of users should identify a common ground of data, plus outlying data items showing possible best and worst practise.

Repeating over time for a single user should show how a user overcomes initial mouse/menu selections with keyboard shortcuts, or gets into bad habits in particular applications (identifying best practice, "Friday afternoon syndrome" or possible training issues).

The combination of the usability metrics in this manor is a unique approach to human computer interaction, which uniquely enhances usability measurement and human factors engineering.

The user metrics: keystroke, mouse clicks, application frequency—and associated data may be used for both business and security applications. The metrics are used to ascertain information regarding several critical business and security applications: Security-Impersonation, Security-Profiling, Business-Training and Coaching, Application Development, and Safety. Other applications may be known to those with ordinary skill in the art.

First, user metrics may be used to determine whether the active user is actually the user who logged on to a workstation. Significant biometric hardware investment has traditionally been used to solve this problem. However, with the methods of the present disclosure, real-time user metrics may assess user behavior to understand if the active user's usage profile matches that of the logged on user. If a discrepancy between profiles is found, a security event may be logged. This event on its own or in combination with other security system alerts can be used to take protective action which may include, but is not limited to, locking access to the work station or forcing the user to re-authenticate security credentials.

In one embodiment, the rate of mouse clicks for the active user using an e-mail window is determined to exceed normal usage associated with the logged on user. In this way, a security alert may be issued notifying the proper personnel that an impersonator has logged on to the system. This is only one illustrative example and many other examples may be known to those with ordinary skill in the art Next, metrics of the present disclosure may be used to determine if the user's activities correspond with their stated role. The traditional approach to security in most instances is a role based security model which allows access rights corresponding to role. While this is an effective model the limitations of it include the fact that many applications may not support the level of restrictions required. Secondly, the fact that there are generally no warnings to indicate if a user has breached their access rights is a severe limitation. An alternative approach is to study user behavior and determine if it is in line with the expected behavior for that role. Analyzing application usage and possibly allowing users to 'stray' beyond their privileged access delivers an insight into what that user may be trying to do. For example a user who is modifying network settings may be trying to bypass a firewall, a user modifying hardware devices may be trying to connect external storage. Preventing these activities forces suspect users to try alternative means with no indication to security personnel that this is occurring. Allowing less restrictive access with strict monitoring delivers detailed insight into user behavior.

Also, the methods of the present disclosure are not limited to security applications, but may also be effective for business applications. In one embodiment, the metrics of the present disclosure determine the level of proficiency with a certain application. Comparing users against their more experienced peers provides detailed analysis of the knowledge gaps in existence and allows training to be targeted to areas that can deliver greatest value. Specifically analyzing how users interact with applications such as frequent window switching, use of mouse versus keyboard, and use of shortcut keys versus menu items will help target speed and efficiency training to users that would benefit from it.

The methods of the application may also be beneficial for software developers. The metrics of the present disclosure enables software developers to gain a greater insight into the utilization of application features and functionality. Comparing the keyboard or mouse click rates of different UI's will help designers improve the usability and efficiency of applications. For example, a software developer working on a new e-mail application may determine, after studying detailed user profiles, that there are not enough keyboard shortcuts in the application since mouse clicks for the new e-mail application are high compared to mouse clicks in a standard e-mail application. This is only one illustrative example and other uses of the metrics may be known to those with ordinary skill in the art.

Finally, safety concerns and alerts may also be raised through the methods of the present disclosure. For example, tracking keyboard and mouse behavior in particular will provide a means to assess a users exposure to Repetitive Strain Injury and the software could be configured to provide prompts to the user either to suggest breaks or to force the user to use an alternative device to clear a message prompt thereby breaking the repetitive cycle of activity.

Monitoring user computer interactions through the methods of the present disclosure allow a greater insight into the way in which a user communicates and interfaces with a computer or other workstation. With this belief in mind, several applications are presented. However, a limitless number of other applications may be known to those with ordinary skill in the art which still rely on and are within the spirit of the disclosure.

Figure 4:
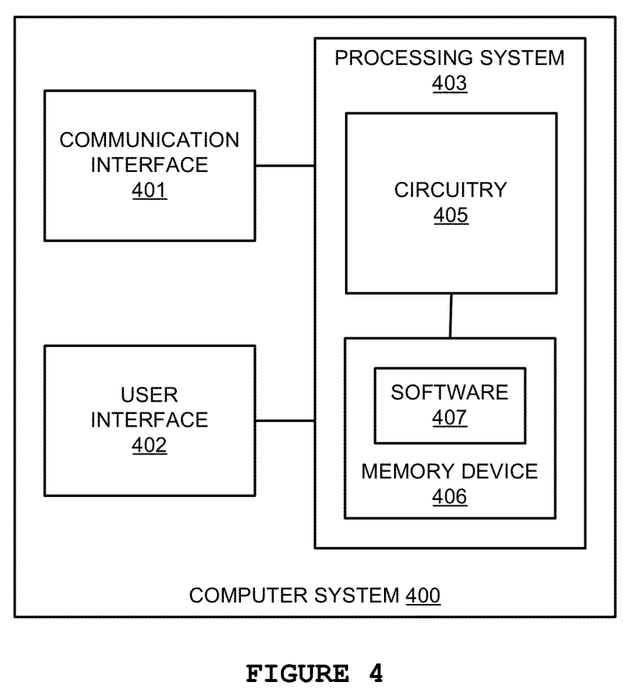
FIG. 4 is a block diagram that illustrates a computer system.

FIG. 4 is a block diagram that illustrates computer system 400. Computer system 400 provides an example of a computer system that may be used to implement aspects of the present disclosure, although such a computer system may use alternative configurations. Computer system 400 comprises communication interface 401, user interface 402, and processing system 403. Processing system 403 is linked to communication interface 401 and user interface 402. Processing system 403 includes processing circuitry 405 and memory device 406 that stores operating software 407.

Communication interface 401 comprises components that communicate over communication links, such as network cards, ports, radio frequency (RF) transceivers, processing circuitry and software, or some other communication components. Communication interface 401 may be configured to communicate over metallic, wireless, or optical links. Communication interface 401 may be configured to use time-division multiplexing (TDM), internet protocol (IP), Ethernet, optical networking, wireless protocols, communication signaling, or some other communication format—including combinations thereof.

User interface 402 comprises components that interact with a user to receive user inputs and to present media and/or information. User interface 402 may include a speaker, microphone, buttons, lights, display screen, touch screen, touch pad, scroll wheel, communication port, or some other user input/output apparatus—including combinations thereof. User interface 402 may be omitted in some examples.

Processing circuitry 405 comprises microprocessor and other circuitry that retrieves and executes operating software 407 from memory device 406. Memory device 406 comprises a disk drive, flash drive, data storage circuitry, or some other memory apparatus. Processing circuitry 405 is typically mounted on a circuit board that may also hold memory device 406 and portions of communication interface 401 and user interface 402. Operating software 407 comprises computer programs, firmware, or some other form of machine-readable processing instructions. Operating software 407 may include an operating system, utilities, drivers, network interfaces, applications, or some other type of software. When executed by circuitry 405, operating software 407 directs processing system 403 to operate computer system 400 as described herein.

It will be apparent to those skilled in the art that various modifications and variations may be made in the above disclosure and aspects of the disclosure without departing from the scope or intent of the disclosure. Other embodiments of the disclosure will be apparent to those skilled in the art from consideration of the specification and practice of the disclosure disclosed herein. It is intended that the specification and examples be considered as exemplary only.

What is claimed is:

1. A method for monitoring, understanding, or modifying user-computer interactions including the steps of:
   monitoring at least one computer application, operating system, or program;
   monitoring at least one user's application characteristics including a rate of switching between said at least one computer application, operating system, or program, wherein said at least one user's application characteristics include a screen frequency comprising a number of times a window associated with said at least one computer application, operating system, or program appears on a screen;
   monitoring said at least one user's application characteristics including a duration said at least one user uses said at least one computer application, operating system, or program;
   monitoring said at least one user's keystroke characteristics in at least one said computer application, operating system, or program;
   monitoring said at least one user's mouse characteristics in said at least one computer application, operating system, or program;
   associating said at least one user's application characteristics, mouse characteristics, and keystroke characteristics to a profile for said at least one user; and
   in a computing system, detecting a change in computer use associated with said at least one user based on a deviation from the profile for said at least one user.

2. The method of claim 1, wherein said step of monitoring said at least one user's keystroke characteristics further includes the step of monitoring said at least one user's keystroke rate.

3. The method of claim 1, wherein said step of monitoring said at least one user's keystroke characteristics further includes the step of monitoring said at least one user's keystroke amount.

4. The method of claim 1, wherein said step of monitoring said at least one user's mouse characteristics further includes the step of monitoring said at least one user's mouse click rate.

5. The method of claim 1, wherein said step of monitoring said at least one user's mouse characteristics further includes the step of monitoring said at least one user's mouse click amount.

6. The method of claim 1, wherein said step of monitoring said at least one user's mouse characteristics further includes the step of monitoring said at least one user's mouse movement.

7. The method of claim 1, further comprising analyzing said profile of said at least one user.

8. The method of claim 7, further comprising analyzing said profile against a profile of an organization to which said at least one user belongs.

9. The method of claim 7, further comprising raising alerts based on said analysis, wherein said alerts comprise at least one security alert, business alert, or safety alert.

10. A non-transitory computer readable medium having encoded thereon a program for monitoring, understanding, or modifying user-computer interactions, wherein said program, when executed by a computing system, directs the computing system to:
    monitor at least one computer application, operating system, or program;
    monitor at least one user's application characteristics including a rate of switching between said at least one computer application, operating system, or program, wherein said at least one user's application characteristics include a screen frequency comprising a number of times a window associated with said at least one computer application, operating system, or program appears on a screen;
    monitor said at least one user's application characteristics including a duration said at least one user uses said at least one computer application, operating system, or program;
    monitor said at least one user's keystroke characteristics in at least one said computer application, operating system, or program;
    monitoring said at least one user's mouse characteristics in said at least one computer application, operating system, or program;
    associate said at least one user's application characteristics, mouse characteristics, and keystroke characteristics to a profile for said at least one user; and
    detect a change in computer use associated with said at least one user based on a deviation from the profile for said at least one user.

11. The non-transitory computer readable medium of claim 10, wherein said program further directs the computing system to monitor said at least one user's keystroke rate.

12. The non-transitory computer readable medium of claim 10, wherein said program directs the computing system to monitor said at least one user's keystroke amount.

13. The non-transitory computer readable medium of claim 10, wherein said program directs the computing system to monitor said at least one user's mouse click rate.

14. The non-transitory computer readable medium of claim 10, wherein said program directs the computing system to monitor said at least one user's mouse click amount.

15. The non-transitory computer readable medium of claim 10, wherein said program directs the computing system to monitor said at least one user's mouse movement.

16. The non-transitory computer readable medium of claim 10, wherein said program directs the computing system to analyze said profile of said at least one user.

17. The non-transitory computer readable medium of claim 16, wherein said program directs the computing system to analyze said profile against a profile of an organization to which said at least one user belongs.

18. The non-transitory computer readable medium of claim 16, wherein said program directs the computing system to raise alerts based on said analysis, wherein said alerts comprise at least one security alert, business alert, or safety alert.

19. A monitoring system comprising:
    a computer system and a plurality of input devices coupled to the computer system, wherein the input devices comprise a keyboard and a mouse;
    the computer system configured to receive a user identifier associated with a user operating the computer system, associate a usage session of the computer system with the user based on the user identifier, monitor an application executing on the computer system during the usage session to determine a duration the application is in focus and a frequency of change in the focus of the application, wherein the frequency of change in the focus of the application includes a screen frequency comprising a number of times a window associated with the application appears on a screen, monitor keystroke characteristics and mouse characteristics of the user associated with the application during the usage session, generate a usage profile based on the duration the application is in focus, the frequency of change in the focus of the application, the keystroke characteristics, and the mouse characteristics monitored during the usage session, wherein the usage profile comprises an indication of usage characteristics of the user for the application, and detect a change in computer use associated with the user based on a deviation from the usage profile.

20. The monitoring system of claim 19, wherein the computer system configured to monitor the keystroke characteristics comprises the computer system configured to monitor a keystroke rate and a keystroke amount performed by the user with the keyboard, and wherein the computer system configured to monitor the mouse characteristics comprises the computer system configured to monitor a mouse click rate, a mouse click amount, and mouse movement performed by the user with the mouse.

* * * * *